United States Patent [19]

Shinpo et al.

[11] Patent Number: 4,581,292

[45] Date of Patent: Apr. 8, 1986

[54] SYNTHETIC AMORPHOUS ZIRCONIUM-BONDED SILICATE AND METHOD FOR MAKING SAME

[75] Inventors: Shozo Shinpo, Hyogo; Tetsuo Fushino, Takasago; Akihiro Hachijo, Kobe; Shozo Ohtsu, Kakogawa, all of Japan

[73] Assignees: Lion Corporation, Tokyo; Taki Chemical Co., Ltd., Kakogawa, both of Japan

[21] Appl. No.: 639,111

[22] Filed: Aug. 9, 1984

[30] Foreign Application Priority Data

Aug. 24, 1983 [JP] Japan .................................. 58-153157

[51] Int. Cl.⁴ ...................... C01B 33/20; C01B 33/32
[52] U.S. Cl. .................................... 428/402; 423/326; 423/332; 423/333; 424/49; 428/404; 526/106
[58] Field of Search ................ 526/106; 428/402, 404; 423/326, 332, 333; 424/49

[56] References Cited

U.S. PATENT DOCUMENTS

| | | | |
|---|---|---|---|
| 4,110,083 | 8/1978 | Benedict | 424/49 |
| 4,122,161 | 10/1978 | Wason | 424/49 |
| 4,170,634 | 10/1979 | Cordon et al. | 424/49 |
| 4,246,137 | 1/1981 | Dombro et al. | 526/106 |
| 4,279,780 | 7/1981 | Dombro | 526/106 |

Primary Examiner—William J. Van Balen
Attorney, Agent, or Firm—Wenderoth, Lind & Ponack

[57] ABSTRACT

The present invention provides a synthetic amorphous zirconium-bonded silicate obtained by reacting, as main starting materials, a water-soluble alkali-metal silicate with an inorganic zirconyl salt and a mineral acid, in which zirconium is bonded to silica at the ratio of $ZrO_2$ to $SiO_2$ being 0.1 to 10 weight percent, which silicate is useful as a dentifrice base material and also as a filler for rubber.

26 Claims, 8 Drawing Figures (x 20000)

⊢—⊣
1 μm (x 20000)

⊢—⊣
1 μm

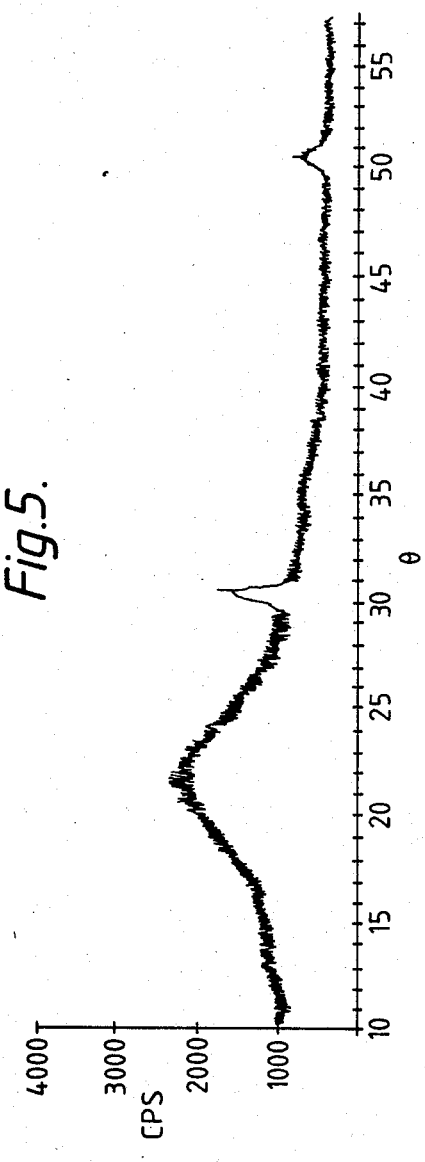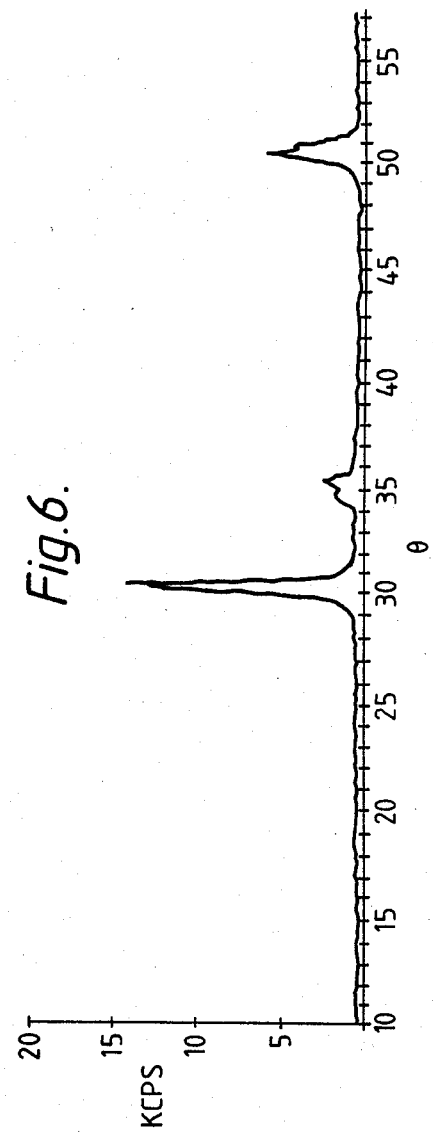

SYNTHETIC AMORPHOUS ZIRCONIUM-BONDED SILICATE AND METHOD FOR MAKING SAME

The present invention relates to a synthetic amorphous zirconium-bonded silicate and to a method of producing the same, and its object is to provide a synthetic amorphous zirconium-bonded silicate useful as a dentifrice base material and also as a filler for rubber.

Up to this time, as an abrasive material especially as a dentifrice material, there has been used fine silicate powder produced by the wet process or the dry process, or natural zirconium silicate. The progress in the method of its production and in the improved technique of its use is surprising. Examples of these are shown in Japanese Patent Publication No. 11159/74, Japanese Patent Kokai Nos. 12869/76 and 136481/76, Japanese Patent Publication No. 36245/82 and many others.

In tooth paste for daily use, the properties required as a dentifrice base material are that it has suitable abrasiveness which does not damage teeth and has suitable liquid absorptivity.

As mentioned above, a method which uses natural zirconium silicate ($ZnSiO_4$) as a dentifrice base material has been proposed. This silicate is of crystalline structure and has a large specific gravity of 4.7 and a high Mohs hardness of 7.5, so that even after being pulverized sufficiently its abrasiveness is so high that it cannot be contained therefor in large amounts in tooth paste. Therefore it has a disadvantage that it cannot hold the shape of tooth paste.

On the other hand, a spherical zirconium-bonded silicate is known in which zirconium and silica are bonded together (Japanese Patent Publication No. 110414/83). Since this silicate is produced from zirconium alcoholate and alkoxysilane in an alkaline organic solvent, its shape is entirely different from that of fine silicate powder produced by the reaction between a water-soluble alkali-metal silicate and a mineral acid, which reaction is known as the wet production process of fine silicate powder. As shown in FIG. 1, its shape is spherical with no primary particles observed. Its shape is completely different from the wet process-produced synthetic amorphous zirconium-bonded silicate (FIG. 2) in which secondary particles are formed from aggregated primary particles. Such a zirconium-bonded silicate with no primary particles being aggregated has no abrasiveness and is not suitable as a tooth paste base material.

Also zirconium-containing silica gel is a known zirconium-containing silicate (Coprecipitation with ruthenium; Report of Mineral Dressing and Smelting Research Institute, Tohoku University, Vol. 35, No. 2, p 93, '79).

This gel producing method starts its reaction from the acid side, and since this silicate is in gel form, no primary particles are observed but glass-like single particles larger than several microns are observed. Accordingly, the zirconium-containing silica gel has a small liquid absorptivity, and when used as a tooth paste base material it cannot give the shape retention necessary for tooth paste. Moreover, this silica gel has so large an abrasiveness that it cannot be contained in large amounts in tooth paste. In this respect, it is not suitable as a tooth paste base material.

Furthermore, a base material for transparent formulation has been proposed in which silica and alumina are bonded with each other (Japanese Patent Publication No. 45411/82 and No. 45412/82). This base material, however, is poor in transparency and stability on standing, and is not always satisfactory.

Moreover, there have been proposed various wet processes for producing precipitated fine silicate powder by reacting a water-soluble alkali-metal silicate solution with a mineral acid to precipitate fine silicate powder, and separating, drying and pulverizing the powder. Also, various processes are actually practiced.

As a general property of precipitated fine silicate powder, its liquid absorptivity and abrasiveness are nearly in inverse proportion. For example, when the liquid absorptivity is 0.8, 1.0 and 1.3 ml/g, the abrasiveness is 55.2, 26.8 and 7.3 mg, respectively.

It is desirable for tooth paste to contain as much base material as possible (for example 30–50%), because when the quantity of base material is little, it shows poor shape retention and assumes a state of "drawing long" though there is some difference depending on the kind of the humectant, binder, etc. contained. Also, such a tooth paste gives a bad feel upon use.

But when the base material is contained in a large quantity, the shape retention is improved, the state of drawing long due to the humectant, binder, etc. is remedied, and the feel upon use also becomes better.

However, as for precipitated fine silicate powder, its property between the liquid absorptivity and abrasiveness is in the above-mentioned relation, and therefore it has not been possible to employ it in large amounts in tooth paste in spite of such a demand.

That is to say, when precipitated fine silicate powder of low liquid absorptivity is used as a base material, it is possible to employ it in large amounts in tooth paste, but since its abrasiveness is large, there is a fear that the tooth paste base material may injure teeth. On the other hand, precipitated fine silicate powder with poor abrasiveness as a tooth paste base material has such a liquid absorptivity that when it is present in large amounts, the viscosity increases to assume a solid form, and the feel upon use becomes bad. As a result, the commodity value of the tooth paste is substantially lowered.

In such a situation, we made various studies to eliminate the above-mentioned property of precipitated fine silicate powder. As a result, we have found that when an inorganic water-soluble zirconyl salt is used upon the production of precipitated fine silicate powder, it is possible to lower the liquid absorptivity and at the same time lower the abrasiveness to a level suitable as a tooth paste base material. We have accomplished the present invention on the basis of this knowledge.

The present invention relates to a synthetic amorphous zirconium-bonded silicate, obtained by reacting, as main starting materials, a water-soluble alkali-metal silicate with an inorganic water-soluble zirconyl salt and a mineral acid, in which zirconium is bonded to silica with $ZrO_2$ to $SiO_2$ ratio being 0.1 to 10 weight %, and the object of the invention is to provide a synthetic amorphous zirconium-bonded silicate which is useful especially as a tooth paste base material.

First, we describe in detail the process for producing the synthetic amorphous zirconium-bonded silicate of the present invention.

As the water-soluble alkali-metal silicates used in the present invention, there can be enumerated sodium, potassium and lithium silicates. However, sodium silicate is most common because of its relatively low price. The water-soluble alkali-metal silicates that can be used are those having a molar ratio SiO$_2$/X$_2$O (wherein X represents alkali-metal) within the range of 2 to 4.

In the present invention, a mineral acid, for example, hydrochloric acid, sulfuric acid, or nitric acid, is used as the acidifying agent for the water-soluble alkali-metal silicate. Particularly important points in the present invention are that the reaction is started from the alkaline side and that zirconium is added in the process of obtaining precipitated fine silicate powder by reacting an alkali-metal silicate solution with a mineral acid. As zirconium-providing substances, it is possible to use the later-mentioned water-soluble zirconyl salts. In the use of the zirconyl salt, there are many ways to add it, for example, zirconyl salt can be added as a water-soluble zirconyl salt solution simultaneously with or separately from other raw materials. However, the best method which we recommend is to add a water-soluble zirconyl salt to a mineral acid to form the zirconium-containing mineral acid, and then to react it with a water-soluble alkali-metal silicate solution. By this method, it is possible to produce the synthetic amorphous zirconium-bonded silicate in a state in which zirconium is bonded very uniformly to silica in comparison with other methods. As water-soluble zirconyl salts used in the present invention, there may be mentioned zirconyl chloride, zirconyl sulfate, zirconyl acetate, etc., but without limitation to these salts. When using a mineral acid containing zirconium, the concentration as zirconia (ZnO$_2$) in the mineral acid is not particularly limited by the concentration, composition, etc. of the water-soluble alkali-metal silicate and the mineral acid which are the starting materials. However, it is desirable to suitably regulate the concentration so that the zirconium in the synthetic amorphous zirconium-bonded silicate will be 0.1-10 weight % as ZrO$_2$ based on SiO$_2$. When the concentration is lower than the lower limit, the effect of addition of zirconium is not remarkable, and when it exceeds the upper limit, an abrasiveness necessary as a tooth paste base material cannot be obtained, and moreover zirconyl hydroxide may be generated depending on the reaction conditions.

As for the reaction of the water-soluble alkali-metal silicate, inorganic water-soluble zirconyl salt and mineral acid, it is important to start the reaction from the alkaline side as mentioned previously. The reason is that if the reaction is started from the acid side, aggregates of primary particles, i.e. secondary particles, are not formed and a gel-like substance having a low liquid absorptivity and an excessive abrasive power is produced.

To start the reaction from the alkaline side as mentioned in the present invention means that the nuclear formation is effected in the alkaline side. For this purpose, there are the following methods, for example:

(1) A method wherein a water-soluble alkali-metal silicate is charged previously in the reaction vessel, and then a water-soluble zirconyl salt and a mineral acid are added thereto to react them;

(2) In a method wherein a water-soluble zirconyl salt-containing mineral acid and a water-soluble alkali-metal silicate are added to the reaction vessel at the same time, the ratio of addition of the water-soluble alkali-metal silicate should be higher than the equivalent of the water-soluble zirconyl-containing mineral acid, so as to always maintain the pH of the reaction mixture above 7.

(3) A method wherein an amount of a water-soluble alkali-metal silicate is charged beforehand in the reaction vessel and then desired amounts of a mineral acid and the water-soluble alkali-metal silicate are added thereto at the same time or separately.

In these methods, the point is to effect the nuclear formation at the alkaline side.

As for the reaction temperature and pH, it is important that the reaction should be carried out at 50°-100° C., and the pH after the completion of the reaction should be 2-8.

When the other reaction conditions are the same, if the temperature is below 50° C., the aggregation of the primary particles becomes difficult, and this degrades the filtering characteristics. On the other hand, when the pH exceeds 8, the precipitation of the synthetic amorphous zirconium-bonded silicate is not effected completely and the reaction yield becomes low, and when the pH is below 2, the product becomes acidified so that the field of application is limited.

As for the concentration of SiO$_2$ in the water-soluble alkali-metal silicate used in this invention, it is desirable to be about 5-15 weight %. Also, as for the acid concentration, it is desirable to be 5-15 weight %, in consideration of the convenience of production. By suitably selecting the other conditions, the concentrations of the starting materials in these ranges can provide the desired physical properties of the synthetic amorphous zirconium-bonded silicate of the present invention.

In the present invention, in order to attain the object more satisfactorily, that is to say to provide the desired abrasiveness, it is useful to make an electrolyte present in the process of precipitating the synthetic amorphous zirconium-bonded silicate wherein an alkali-metal silicate solution is reacted with a zirconium-containing mineral acid.

The synthetic amorphous zirconium-bonded silicate obtained by reacting a mineral acid and an alkali-metal silicate solution in the presence of an electrolyte, has a higher abrasiveness in comparison with the precipitated fine silicate powder obtained in the absence of an electrolyte. This tendency is nearly in proportional relation within a given amount of the electrolyte. That is to say, with the increase in the amount of the electrolyte used, the abrasiveness increases. As previously mentioned, however, since the liquid absorptivity and abrasiveness are nearly in inverse proportion, the adjustment of the liquid absorptivity and abrasiveness to desired values cannot be attained by altering the reaction conditions such as concentrations of the starting materials, reaction temperature, reaction pH, rate of stirring, etc.

On the other hand, in the present invention, it is possible, by the use of a zirconyl salt, to produce a synthetic amorphous zirconium-bonded silicate having a smaller liquid absorptivity and lower abrasiveness in comparison with the case of using no zirconyl salt. However, when the precipitated fine silicate powder resulting from non-use of a zirconyl salt has a low abrasiveness and a high liquid absorptivity, there is no way to provide a higher abrasiveness. In such a case, when a mixture of a suitable ratio of an electrolyte and a zirconyl salt is used, it is possible to produce a synthetic amorphous zirconium-bonded silicate having a desired abrasiveness and a low liquid absorptivity.

In this sense the utilization of electrolytes is very useful for the present invention.

As for the electrolytes used in the present invention, mineral acid salts of water-soluble alkali-metals are preferable, such as mineral acid salts of sodium, potassium, etc. It is also possible to mention sodium chloride, potassium chloride, sodium sulfate, potassium sulfate, sodium nitrate, potassium nitrate, etc. The suitable amount of the electrolyte to be used is within the range of 5 to 60 weight % based on $SiO_2$, by reason of the relation to the abrasiveness of the synthetic amorphous zirconium-bonded silicate. As an actual mode of practice, it is desirable to make an electrolyte contained previously in the alkali-metal silicate solution in respect to providing the abrasiveness of the synthetic amorphous zirconium-bonded silicate. However, it is also possible to add an electrolyte to the mineral acid by suitably selecting the amount of the electrolyte, reaction temperature, reaction time, etc.

In producing the synthetic amorphous zirconium-bonded silicate of the present invention, the point of attention, in addition to starting the reaction from the alkaline side, is to add a zirconyl salt during the process before the silica ($SiO_2$) portion in the water-soluble alkali-metal silicate solution is completely precipitated. Desirably, it is preferred the the water-soluble zirconyl salt be present in the mineral acid. That is to say, even if the water-soluble zirconyl salt is added after the precipitation of the whole silica has been completed, it is impossible to obtain the amorphous zirconium-bonded silicate of the present invention. For example, in the method in which a water-soluble alkali-metal silicate solution and a mineral acid are added at the same time, the water-soluble zirconyl salt should be added before the addition of the former has been finished. After the addition of the water-soluble zirconyl salt has been completed, the mineral acid is added to a desired pH value depending on the desired use.

The production conditions in the present invention are not particularly limited. According to the desired physical properties of the synthetic amorphous zirconium-bonded silicate, the reaction is carried out for 30 minutes to 4 hours under stirring at a reaction temperature of 60°–100° C. in the case of the addition of an electrolyte. The pH at the time of the completion of the reaction should be 2–8.

After the completion of the reaction, filtration and water-washing are conducted in the usual way. The synthetic amorphous zirconium-bonded silicate is separated from the liquid, and then dried and pulverized to obtain the product.

In the thus-obtained synthetic amorphous zirconium-bonded silicate zirconium and silica are bonded in the range of 0.1–10 weight % of zirconium as $ZrO_2$, based on $SiO_2$. The average particle diameter of its primary particles is 0.01–0.5 μm. The surface area by the BET method is 5–800 $m^2/g$, and that by the CTAB method is 5–300 $m^2/g$. The apparent specific gravity is 0.1–0.9 g/ml. The liquid absorptivity is 0.4–2.8 ml/g. The micropore volume is 0.5–6.0 cc/g. When this synthetic amorphous zirconium-bonded silicate is used especially as a dentifrice base material, the liquid absoptivity is little, and its abrasiveness is regulated in a proper range, so that it is possible to employ it in large amounts in tooth paste and the shape retention of the tooth paste can be improved remarkably.

The physical properties which the synthetic amorphous zirconium-bonded silicate of the present invention has, as illustrated concretely, are generally as follows:

REFERENCE 1

Ten kg of an aqueous solution of sodium silicate ($Na_2O.3.1SiO_2$) containing 100 g/kg $SiO_2$ was put into a 20 liter reaction vessel having baffle plates and equipped with a stirrer having a turbine blade of 150 mm diameter, and the reaction temperature was maintained at 87° C. In order to obtain synthetic amorphous zirconium-bonded silicates of different zirconia contents as shown in Table 1, 3688 g solutions of 10% sulfuric acid each containing zirconyl chloride with a different zirconia concentration, were added at a flow rate of 83 g/min, respectively. Then a solution of 10% sulfuric acid was added at a flow rate of 83 g/min. When the pH of the reaction system became 2.8, the addition of the acid was stopped, and the reaction system was aged for 15 minutes After repeating filtration and water-washing, the resulting substance was dried in a drier maintained at 110° C., and then pulverized to obtain a synthetic zirconium-bonded silicate.

On the other hand, instead of the aqueous solution of sodium silicate, an aqueous solution of sodium hydroxide containing 33 g/kg $Na_2O$ was used, and following the above-mentioned method, zirconyl hydroxide ($ZrO(OH)_2$) was obtained. This zirconyl hydroxide was mixed uniformly with the precipitated fine silicate powder containing no zirconium shown in Table 1 to obtain mixtures of precipitated fine silicate powder and zirconyl hydroxide, of different zirconyl contents.

The physical properties of the thus-obtained synthetic amorphous zirconium-bonded silicates, precipitated fine silicate powder (Comparative example) and its mixtures with zirconyl hydroxide are shown in Table 1.

TABLE 1

|  | $ZrO_2/SiO_2$ (wt %) | Liquid absorptivity (ml/g) | Abrasion loss (mg/g) | Refractive index | Minimum turbidity | Ignition loss (%) | Zirconium elution (%) | Specific surface area ($m^2/g$) BET | CTAB | Av. diam. of primary particles (μ) | Av. diam. of aggregated particles (μ) | Apparent specific gravity (g/ml) | Micropore vol. cc/g |
|---|---|---|---|---|---|---|---|---|---|---|---|---|---|
| Examples of the invention | 0.07 | 1.81 | 0.8 | 1.462 | 0.01 | 4.8 | 9.8 | 405 | 158 | 0.02 | 5.8 | 0.24 | 3.7 |
|  | 0.50 | 1.78 | 0.7 | 1.464 | 0.01 | 5.2 | 11.1 | 448 | 174 | 0.02 | 6.1 | 0.22 | 3.5 |
|  | 2.0 | 1.73 | 0.4 | 1.468 | 0.01 | 5.8 | 27.3 | 562 | 209 | 0.01 | 5.4 | 0.25 | 3.1 |
| Comparative example | 0 | 1.82 | 0.8 | 1.461 | 0.01 | 4.5 | 0 | 383 | 152 | 0.02 | 5.6 | 0.20 | 3.8 |
| Mixtures | 0.07 | 1.82 | 0.8 | 1.461 | 0.15 | 4.5 | 81.2 | 391 | 156 | 0.02 | 5.6 | 0.20 | 3.8 |
|  | 0.50 | 1.82 | 0.7 | 1.461 | 0.52 | 4.6 | 80.6 | 367 | 148 | 0.02 | 5.5 | 0.20 | 3.9 |
|  | 2.0 | 1.80 | 0.8 | 1.461 | 0.96 | 4.7 | 79.9 | 372 | 141 | 0.02 | 5.7 | 0.22 | 3.7 |

REFERENCE 2

The same experiment was carried out as in Reference 1 except that, in place of the aqueous solution of sodium silicate and the aqueous solution of sodium hydroxide, an aqueous solution of sodium silicate containing 20 g/kg NaCl and an aqueous solution of sodium hydroxide containing 20 g/g NaCl were used.

The physical properties of the thus-obtained synthetic amorphous zirconium-bonded silicates, precipitated fine silicate powder (comparative example) and its mixtures with zirconyl hydroxide are shown in Table 2.

medium by means of a vacuum mixer for 10 minutes, under defoaming.

The refractive index and the turbidity of this mixture at 25° C. are measured. By plotting the measured data, a refractive index-turbidity curve is obtained. The refractive index of this mixture when the turbidity is minimum is taken as the refractive index of the sample.

For the measurement of the refractive indices, an Abbe's refractometer is used, and for the measurement of turbidity an integrating sphere turbidimeter is used. The turbidity is obtained from the percent transmission of the sample 1 mm thick.

As for samples having refractive indices higher than

TABLE 2

| | $ZrO_2/SiO_2$ (wt %) | Liquid absorptivity (ml/g) | Abrasion loss (mg/g) | Refractive index | Minimum turbidity | Ignition loss (%) | Zirconium elution (%) | Specific Surface area ($m^2/g$) BET | Specific Surface area ($m^2/g$) CTAB | Av. diam. of primary particles ($\mu$) | Av. diam. of aggregated particles ($\mu$) | Apparent specific gravity (g/ml) | Micro pore vol. cc/g |
|---|---|---|---|---|---|---|---|---|---|---|---|---|---|
| Examples of the invention | 0.07 | 1.02 | 1.73 | 1.462 | 0.03 | 5.1 | 9.1 | 340 | 35 | 0.22 | 8.1 | 0.50 | 1.2 |
| | 0.50 | 0.93 | 13.1 | 1.464 | 0.04 | 5.3 | 10.4 | 382 | 63 | 0.20 | 7.8 | 0.56 | 1.1 |
| | 2.0 | 0.81 | 7.4 | 1.468 | 0.05 | 5.8 | 25.6 | 453 | 115 | 0.14 | 8.5 | 0.61 | 0.9 |
| Comparative example | 0 | 1.06 | 19.8 | 1.461 | 0.03 | 4.7 | 0 | 325 | 27 | 0.23 | 8.2 | 0.48 | 1.3 |
| Mixtures | 0.07 | 1.05 | 20.3 | 1.461 | 0.18 | 4.7 | 80.2 | 316 | 30 | 0.23 | 8.2 | 0.48 | 1.3 |
| | 0.50 | 1.05 | 19.5 | 1.461 | 0.55 | 4.8 | 79.1 | 342 | 23 | 0.23 | 7.8 | 0.47 | 1.3 |
| | 2.0 | 1.03 | 20.7 | 1.461 | 0.96 | 4.9 | 81.0 | 332 | 26 | 0.23 | 8.1 | 0.49 | 1.3 |

To explain the present invention in further detail, the terms (X-ray diffraction, liquid absorptivity, abrasion loss, refractive index, minimum turbidity, ignition loss, percent zirconium elution, surface area by the BET method, surface area by the CTAB method, average diameter of primary particles, average diameter of aggregated particles, apparent specific gravity and micropore volume) used in the present invention are explained in the following.

(1) X-ray diffraction

As the X-ray diffractometer, a Geigerflex RAD-IA type X-ray diffractometer produced by Rigaku Denki K. K. was used. Part of the samples were heat-treated beforehand at 900° C. for one hour for the purpose of comparing crystalline forms.

(2) Liquid absoptivity 1.0 g of a sample is weighed out and placed on a glass plate. While adding a 47.5% aqueous glycerin solution bit by bit from a 5 ml microburette, the sample and the glycerin solution are uniformly mixed by a stainless steel spatula so that the solution can extend to the whole. The addition is continued until the sample becomes granular and further forms a mass of solid paste and yet the mixture does not become sticky with respect to the glass plate. This time is the end point of the addition. The quantity (ml) required is converted to the quantity of liquid absorption per anhydrous sample.

(3) Abrasion loss

An amount of an aqueous 60% glycerin solution containing 25% fine silicate powder is placed on a smooth brass plate and the plate is abraded 18,000 times by a horizontally reciprocating brushing abrasion tester under a load of 500 g. The weight loss of the brass plate is the abrasion loss.

(4) Refractive index

Glycerin and water are mixed in various ratios to prepare disperse media having various refractive indices. 15 g of a sample is dispersed in 35 g of each disperse 1.47, mixtures of methylene iodide with alcohols such as ethanol, propanol, isopropanol, etc. were used as disperse in media.

(5) Ignition loss

Two grams of a sample is put into a platinum crucible, and after drying it at 105° C. for 2 hours, the sample weight ($W_1$) is measured. After heating it at 900° C. in an electric furnace for one hour, it is allowed to cool in a desiccator. The sample weight ($W_2$) is then measured. The ignition loss is obtained from the following formula:

$$\text{Ignition loss (\%)} = \frac{W_1 - W_2}{W_1} \times 100$$

(6) Percent zirconium elution

Two grams of a sample are put into a tall beaker of 300 ml capacity, and 100 ml of 2N hydrochloric acid is added. The mixture is boiled for one hour and after cooling, it is filtered through a no. 5C filter. The filtrate is put into a 250 ml messflask and is used as the solution for test. The analysis of zirconium is conducted by the colorimetry using arsenazo, and the quantity of eluted zirconium (a grams) per gram sample is obtained.

On the other hand, one gram of the sample is taken on a platinum dish, and 10 ml water, 0.5 ml 50% sulfuric acid and 10 ml hydrofluoric acid are added. After the sample is evaporated to dryness on a sand bath, the zirconium content (b grams) per gram sample is obtained, following the above-mentioned method. Percent zirconium elution is calculated according to the following formula:

$$\text{Percent zirconium elution} = \frac{a}{b} \times 100$$

(7) Measurement of the specific surface area by the BET method

Liquid nitrogen is used as the coolant. From the quantity of nitrogen gas adsorption at $-196°$ C., the surface area per gram anhydride is calulated by the BET method, wherein the sectional area of a nitrogen molecule is assumed to be 16.2 Å$^2$. The degassing of the sample is carried out at 140° C. under a vacuum of $1 \times 10^{-5}$ mmHg for 60 minutes.

(8) Measurement of the specific surface area by the CTAB method

Cetyl methyl ammonium bromide (CTAB) is caused to be adsorbed to saturation on the surface of a sample in an aqueous solution of the bromide. The surface area per gram anhydride is calculated from adsorbed quantity, wherein the cross-sectional area of the bromide is assumed to be 35 Å$^2$.

One gram of a sample of a known moisture content is weighed out into a 300 ml Erlenmeyer flask having a ground stopper, and 100 ml of a 0.55% CTAB solution is added. After adjusting the pH of the solution to 9.0 with a N/10 NaOH solution, the mixture is stirred with a magnetic stirrer for two hours.

The suspension is sedimented by centrifugation, and 10 ml of the supernatant is taken into a 300 ml Erlenmeyer flask to use for titration. Fifty ml. ion-exchanged water, 25 ml chloroform, and bromophenol blue indicator are added. The solution is then titrated with a sodium dioctyl sulfosuccinate solution (Aerosol OT) which has been previously standardized with a CTAB standard solution. The titration volume ($V_2$) of the Aerosol OT solution is obtained, the end point being the time at which the chloroform layer becomes colorless and the water layer becomes slightly purplish.

Ten ml of the CTAB solution before the adsorption operation is then titrated by the same operation to obtain the titration volume ($V_1$) of the Aerosol OT solution.

The surface area per gram anhydride (S m$^2$/g) is calculated from the following formula:

$$S = \frac{5.78 \times (V_1 - V_2) \times a}{X}$$

wherein X is the weight (g) of the sample converted to anhydride, and a is the weight (mg) of CTAB corresponding to 1 ml of the Aerosol solution.

(9) Average diameter of primary particles

The arithmetical average value of the unit particle diameters is obtained by the observation through a scanning type electron microscope.

(10) Average diameter of aggregated particles

By means of a measuring apparatus of particle size distribution of centrifugal sedimentation type (SA-CP 2 type) produced by Shimadzu Seisakusho, Ltd., and using water as the dispersion medium, the particle size distribution is measured. The particle diameter at which the cumulative distribution is 50 weight percent is taken as the average diameter of aggregated particles.

(11) Apparent specific gravity

Ten grams of a sample is weighed out into a graduated glass tube having an inner diameter of 30 mm and a capacity of 100 ml. After tapping the glass tube 500 times by dropping it from a height of 10 mm, the volume of the sample is measured. The apparent specific gravity is obtained from the following formula:

Apparent specific gravity (g/ml) = $\frac{\text{Weight (g) of the sample}}{\text{Volume (ml) of the filled sample}}$

(12) Micropore volume

By means of a porosimeter (Pore Sizer 9300, produced by Shimadzu Seisakusho, Ltd.) and by the mercury penetration method under a pressure of 0–30,000 psia, the total micropore volume is measured.

In FIG. 3 is shown the X-ray diffraction pattern of a synthetic amorphous zirconium-bonded silicate (hereinafter called the silicate of the invention) containing 2.97% ZrO$_2$, and in FIG. 4 is shown the X-ray diffraction pattern of the heat-treated silicate of the invention. In FIG. 5 is shown the X-ray diffraction pattern of a mixture of precipitated fine silicate powder and zirconyl hydroxide (hereinafter called the mixture) containing 28% ZrO$_2$, which has been heat-treated. In FIG. 6 is shown the X-ray diffraction pattern of heat-treated zirconyl hydroxide. In FIG. 7 is shown the X-ray diffraction pattern of zircon flower (zirconium silicate). In FIG. 8 is shown the X-ray diffraction pattern of a mixture of zircon flower and precipitated fine silicate powder.

As apparent from FIGS. 3 and 4, the silicate of the invention, either non-heat-treated or heat-treated, takes an amorphous form. In comparison with FIGS. 5 and 6, in which diffraction peaks appear, the silicate of the invention does not show such diffraction peaks.

Also as apparent from FIGS. 7 and 8, the X-ray diffraction pattern of the silicate of the invention is also different from that of the mixture of precipitated fine silicate powder and zirconium silicate which has peaks. This shows that the silicate of the invention is not a mixture of these silicates.

From these results of X-ray diffraction, it is acknowledged that, in the silicate of the invention, zirconium is dispersed uniformly while bonded to silica.

As apparent from Tables 1 and 2, no substantial decrease in liquid absorptivity is observed in the case of the mixture. But in the silicate of the invention, the liquid absorptivity as well as the abrasion loss decreases with the increase of the content of zirconium.

Furthermore, the silicate of the invention shows a tendency of decreasing the micropore volume and increasing the apparent specific gravity with the increase of zirconium content. In the general precipitated fine silicate powder, such a phenomenon tends to increase the abrasiveness However, contrary to expectation, in the silicate of the invention the abrasiveness decreases inversely.

It is not exactly known why the abrasiveness decreases with the decrease of the liquid absorptivity and the micropore volume, and with the increase of the apparent specific gravity. However, in view of the fact that there is a tendency of decreasing the average diameter of the primary particles with the increase of zirconium content, it is supposed that the zirconium plays a great role upon the formation of the primary particles or the aggregated particles of the silicate of the invention.

It is also understood that the zirconium is dispersed uniformly in the interior of the silicate, from the fact that the refractive index varies with the zirconium content, without increase of turbidity.

The silicate of the present invention obtained by reacting a water-soluble alkali-metal silicate with an inorganic water-soluble zirconyl salt and a mineral salt, is very important as a base material for transparent dentifrice. Such a base material has not been obtainable from the conventional fine silicate powder.

It is seen that the ignition loss of the silicate of the present invention is very high in comparison with that of the mixture. It is generally believed that the ignition loss of fine silicate powder is in proportion to the amount of the hydroxyl groups to be separated from the surface of silica. Therefore, the ignition loss method is a technique utilized to determine the amount of the hydroxyl groups on the surface of silica. Accordingly, an increase in the amount of ignition loss means an increase of silanol groups (Si—OH). Thus, in the process of the present invention, it is presumed that zirconium hinders the formation of siloxane bonds (Si—O—Si).

Since such a phenomenon cannot be explained from mere adhesion or adsorption of zirconium, it is conjectured that zirconium forms some bond with silica.

As a phenomenon that permits such a conjecture, it is possible to illustrate the percent zirconium elution. As apparent from Tables 1 and 2, the percent zirconium elution by hydrochloric acid from the silicate of the invention is remarkably low, whereas that of the mixture is remarkably high.

This fact means that zirconium forms some type of bond with silica.

Also the silicate of the invention has an increased specific surface area of both the BET method and the CTAB method with the increase in zirconium content, and therefore it is seen that it is useful also as a filler for rubber.

The silicate of the invention has such physical properties as explained above and is useful as a base material for dentifrice, especially as a base material for a transparent dentifrice. In addition, when it is used as a filler for rubber, it exhibits an extremely advantageous effect as shown in the Examples. As apparent from the explanation made hereinabove, the silicate of the invention can be used not only as a base material for dentifrice and a filler for rubber but also like the usual precipitated fine silicate powder, it can be used, of course, as a paint, sedimentation preventing agent for ink, carrier for agricultural chemicals, filler for plastics, heat resisting agent for fats and oils, emulsifier for cosmetics, delustering agent for paper, adhesive, heat insulator, agent for making adhesives transparent, etc.

In the following the present invention is explained by way of Examples:

EXAMPLE 1

Ten kg of sodium silicate ($Na_2O.2.8SiO_2$) containing 95 g/kg silicate and NaCl as in Table 3 was put into a 20 liter reaction vessel having baffle plates and equipped with a stirrer having a turbine blade of 150 mm diameter, and the reaction temperature was maintained at 80° C. In order to obtain the silicates of the present invention having different zirconia contents as shown in Table 3, 3879 g of 10% sulfuric acid solutions each containing zirconyl sulfate with a different zirconia concentration were added at a flow rate of 61 g/min, respectively. Then a solution of 10% sulfuric acid was added at a flow rate of 61 g/min. When the pH of the reaction system became 5.8, the addition of the acid was stopped, and the reaction system was aged for 20 minutes.

After repeating filtration and water-washing, the resulting substance was dried in a drier maintained at 110° C., and then pulverized to obtain the silicate of the present invention. The physical properties of the thus-obtained silicates are shown in Table 3.

The silicates of the invention were subjected to X-ray diffraction analysis. The result showed that the silicates, both non-heat-treated and heat-treated (900° C., one hour) were amorphous.

TABLE 3

| $NaCl/SiO_2$ (wt %) | $ZrO_2/SiO_2$ (wt %) | Liquid absorptivity (ml/g) | Abrasion loss (mg/g) | Refractive index | Specific surface area ($m^2$/g) BET | Specific surface area ($m^2$/g) CTAB | Average diam. of primary particles ($\mu$) | Average diam. of aggregated particles ($\mu$) | Apparent specific gravity (g/ml) | Micropore volume (cc/g) |
|---|---|---|---|---|---|---|---|---|---|---|
| 0 | 0 | 1.96 | 0.4 | 1.452 | 186 | 142 | 0.02 | 5.4 | 0.15 | 4.5 |
|  | 0.3 | 1.95 | 0.4 | 1.459 | 274 | 157 | 0.02 | 5.8 | 0.16 | 4.4 |
|  | 1.0 | 1.92 | 0.3 | 1.460 | 310 | 193 | 0.01 | 5.1 | 0.17 | 4.1 |
|  | 5.0 | 1.87 | 0.3 | 1.465 | 382 | 238 | 0.01 | 5.9 | 0.21 | 3.7 |
| 10 | 0 | 1.52 | 2.7 | 1.444 | 953 | 48 | 0.09 | 7.2 | 0.35 | 1.6 |
|  | 0.3 | 1.48 | 2.4 | 1.458 | 258 | 55 | 0.09 | 7.8 | 0.37 | 1.5 |
|  | 1.0 | 1.39 | 1.8 | 1.461 | 291 | 94 | 0.08 | 6.9 | 0.41 | 1.4 |
|  | 5.0 | 1.30 | 1.1 | 1.464 | 354 | 152 | 0.05 | 7.5 | 0.48 | 1.3 |
| 25 | 0 | 1.11 | 15.6 | 1.440 | 127 | 28 | 0.20 | 7.3 | 0.48 | 1.2 |
|  | 0.3 | 1.05 | 13.1 | 1.458 | 284 | 41 | 0.20 | 8.1 | 0.52 | 1.1 |
|  | 1.0 | 0.93 | 7.7 | 1.461 | 303 | 69 | 0.17 | 8.8 | 0.59 | 0.9 |
|  | 5.0 | 0.78 | 3.4 | 1.462 | 368 | 133 | 0.10 | 7.9 | 0.68 | 0.7 |
| 50 | 0 | 0.95 | 38.8 | 1.435 | 116 | 15 | 0.32 | 8.5 | 0.62 | 1.0 |
|  | 0.3 | 0.89 | 32.1 | 1.458 | 252 | 29 | 0.31 | 9.2 | 0.65 | 0.9 |
|  | 1.0 | 0.78 | 20.3 | 1.460 | 289 | 53 | 0.23 | 8.7 | 0.76 | 0.8 |
|  | 5.0 | 0.63 | 8.6 | 1.463 | 332 | 91 | 0.13 | 9.5 | 0.81 | 0.7 |

As apparent from Table 3, it is seen that the silicates, of which the liquid absorptivity was reduced by the addition of the electrolyte, have an increased abrasion loss, whereas as for the silicates of the invention, both the liquid absorptivity and the abrasion loss are decreased with the increase of zirconia content. Such characteristics make it possible for tooth paste to contain a large amount of base material, and moreover are useful for obtaining a tooth paste having a suitable abrasiveness which does not injure teeth.

The silicates of the invention obtained in the absence of an electrolyte have an increased specific surface area by both the BET and CTAB methods with the increase of zirconium content. Therefore they are also useful as a filler for rubber. Besides they can be used as a paint, sedimentation preventing agent for ink, carrier for agricultural chemicals, filler for plastics, etc.

EXAMPLE 2

Three kg of an aqueous solution of potassium sulfate containing 67 g potassium sulfate was placed in the reaction vessel used in Example 1, and the reaction temperature was maintained at 75° C.

Then the addition of an aqueous solution of potassium silicate ($K_2O.3.1SiO_2$) containing 120 g/kg $SiO_2$, an aqueous solution of zirconyl sulfate containing 10 g/kg $ZrO_2$ and an aqueous solution of 8% hydrochloric acid, was started at the same time at a flow rate of 106 g/min, 5.1 g/min and 44 g/min, respectively. After the addition of the aqueous potassium silicate solution and the aqueous zirconyl sulfate was finished, the addition of the aqueous 8% hydrochloric acid solution was further continued, and when the pH of the reaction system reached 7.2, the addtion of the acid was stopped, and the reaction system was aged at 95° C. for 20 minutes.

After repeating filtration and water-washing, the resulting substance was dried in a drier maintained at 110° C., and then pulverized to obtain the silicate of the invention.

The physical properties of the thus-obtained silicate of the invention were as follows:

Average primary particle diameter: 0.05 μm,
average aggregated particle diameter: 9.2 μm,
specific surface area by the BET method: 43 m²/g,
specific surface area by the CTAB method: 38 m²/g,
apparent specific gravity: 0.45 g/ml,
liquid absorptivity: 0.86 m²/g,
refractive index: 1.438,
micropore volume: 1.1 cc/g.

The silicate of the invention had a suitable abrasiveness as a base material for a dentifrice.

EXAMPLE 3

Ten kg of an aqueous solution of sodium silicate ($Na_2O.2.8SiO_2$) containing 110 g/kg $SiO_2$ was placed in the reaction vessel used in Example 1, and the reaction temperature was maintained at 60° C. In order to obtain the silicates of the invention having different zirconia contents as in Table 4, 4492 g solutions of 10% sulfuric acid each containing zirconyl chloride with a different zirconia concetration were added at a flow rate of 106 g/min.

Then 10% sulfuric acid was added at a flow rate of 106 g/min. When the pH of the reaction system reached 5.3, the addition of the acid was stopped and the reaction system was aged at 95° C. for 30 minutes.

After repeating filtration and water-washing, the resulting substance was dried in a drier maintained at 110° C. and was pulverized to obtain the silicate of the invention.

The thus-obtained silicate of the invention was mixed with styrene-butadiene rubber in the ratio of 1:2. After vulcanization at 140° C., the tensile strength and 300% tensile stress were measured. The results are shown in Table 4.

The silicates of the invention were subjected to X-ray diffraction analysis. The result showed that the silicates, both non-heat-treated and heat-treated (900° C., one hour) were amorphous.

TABLE 4

| $ZrO_2/SiO_2$ | Tensile strength (kg/cm³) | 300% tensile stress (kg/cm³) |
|---|---|---|
| 0 | 246 | 67 |
| 1 | 264 | 88 |
| 2 | 288 | 102 |

As apparent from Table 4, the silicates of the invention have an increased tensile strength and an increased 300% tensile stress with the increase of zirconia content. Such characteristics seem to be related to the fact that the silicates of the invention have a large amount of silanol groups and a large specific surface area by the CTAB method, as mentioned above. From such characteristics it is seen that the silicates of the invention are useful as a reinforcing material for rubber.

BRIEF EXPLANATION OF THE DRAWINGS

FIG. 5 is the X-ray diffraction pattern of a heat-treated mixture of precipitated fine silicate powder and zirconyl hydroxide.

FIG. 6 is the X-ray diffraction pattern of heat-treated zirconyl hydroxide.

Figure 1:
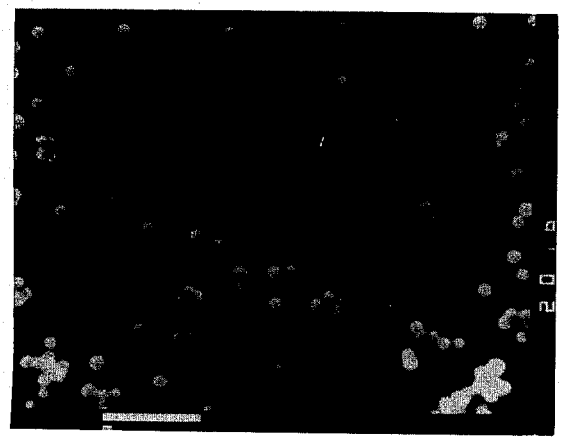
FIG. 1 is a microscopic photograph of a globular zirconium-bonded silicate in which zirconium and silica are bonded together.
Figure 2:
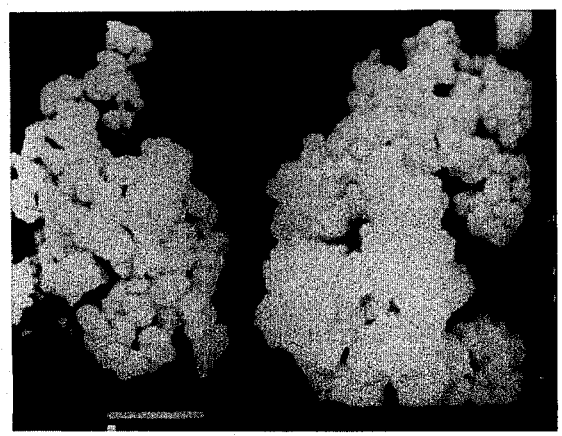
FIG. 2 is a microscopic photograph of a synthetic amorphous zirconium-bonded silicate of the invention.
Figure 3:
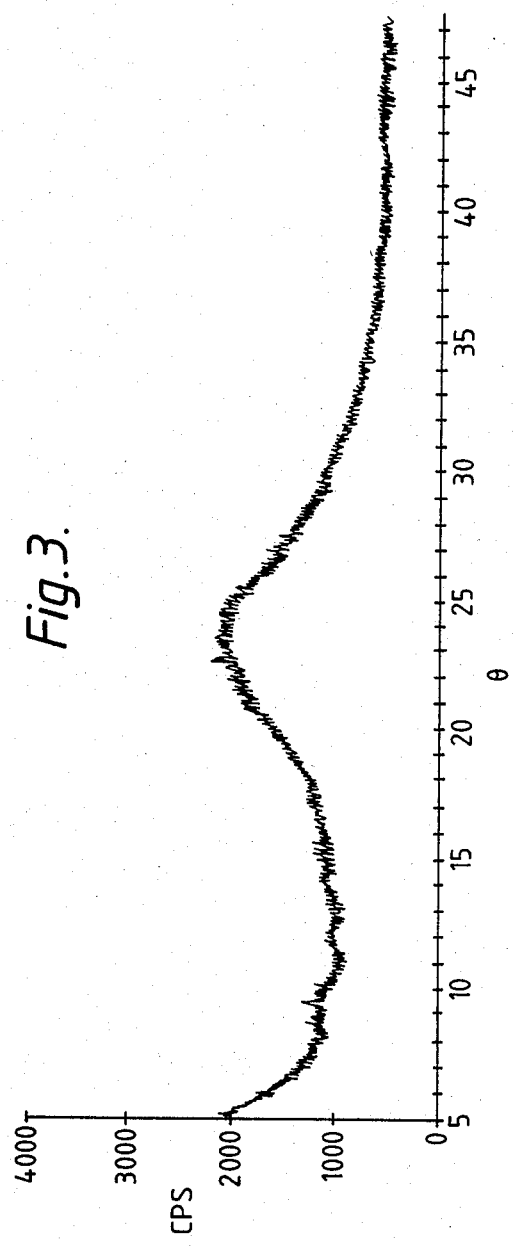
FIG. 3 is the X-ray diffraction pattern of a synthetic amorphous zirconium-bonded silicate of the invention.
Figure 4:
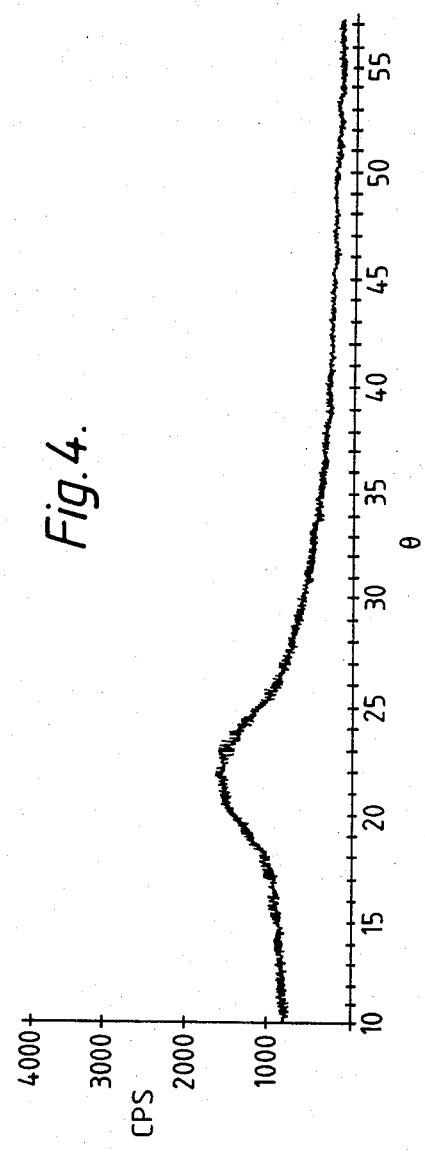
FIG. 4 is the X-ray diffraction pattern of a synthetic amorphous zirconium-bonded silicate of the invention which has been heat-treated.
Figure 7:
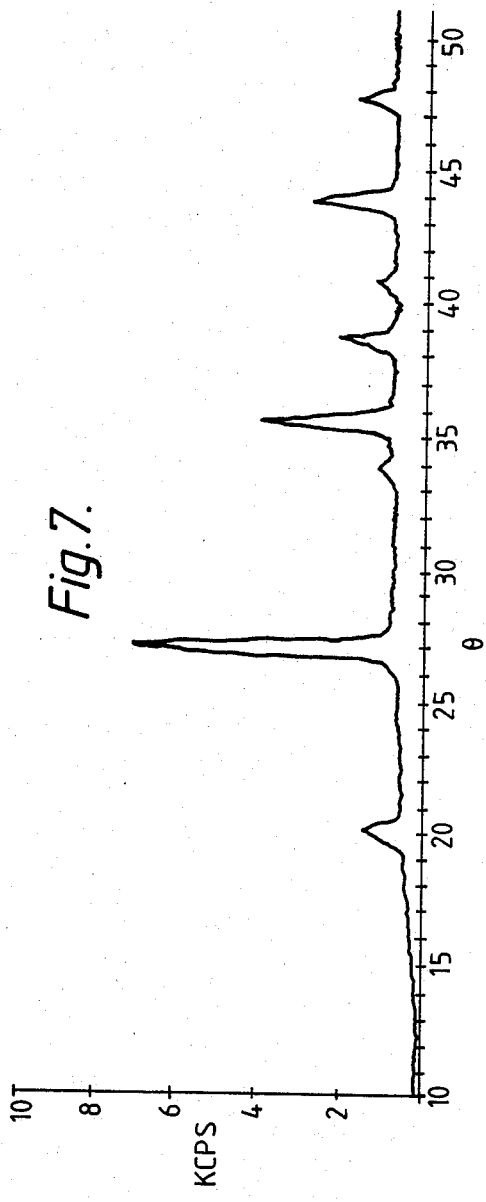
FIG. 7 is the X-ray diffraction pattern of zircon flower (zirconium silicate).
Figure 8:
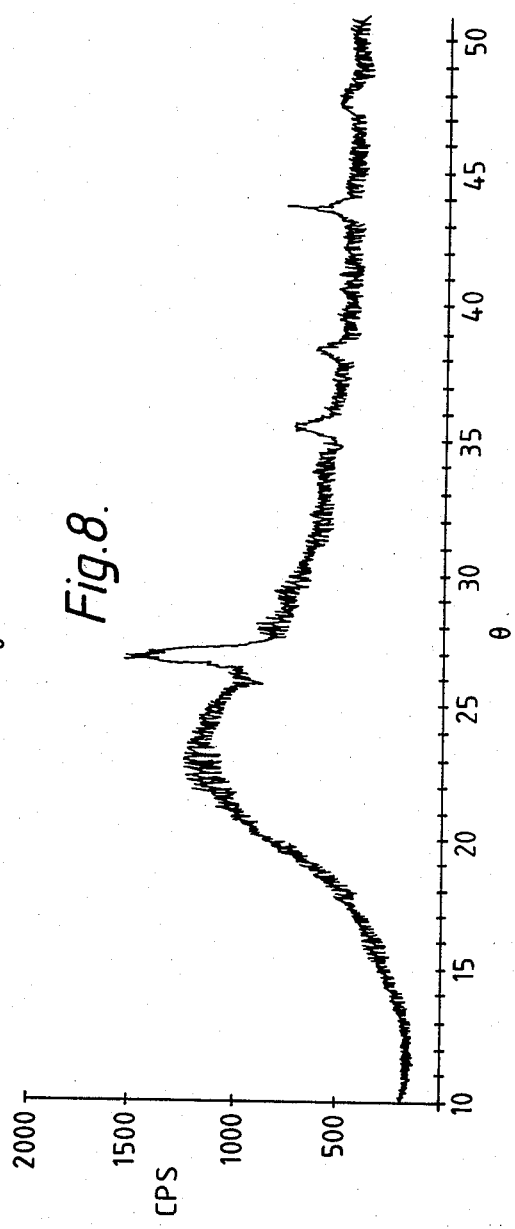
FIG. 8 is the X-ray diffraction pattern of a mixture of zircon flower and precipitated fine silicate powder.

What is claimed is:

1. A synthetic amorphous zirconium-bonded silicate obtained by reacting, as main starting materials, a water-soluble alkali-metal silicate with an inorganic zirconyl salt and a mineral acid, in which zirconium is bonded to silica at the ratio of $ZrO_2$ to $SiO_2$ being 0.1 to 10 weight percent and wherein the synthetic amorphous zirconium-bonded silicate contains aggregated particles composed of primary particles, the average particle diameter of the primary particles of said silicate being 0.01 to 0.5 μm and the average particle diameter of the aggregated particles being 1.5 to 30 μm.

2. The silicate as claimed in claim 1 obtained by starting the reaction from the alkaline side.

3. The silicate as claimed in claim 1, of which the specific surface area by the BET method is 5 to 800 m²/g, and the specific surface area by the CTAB method is 5 to 300 m²/g.

4. The silicate as claimed in claim 1, of which the apparent specific gravity if 0.1 to 0.9 g/ml.

5. The silicate as claimed in claim 1, of which the liquid absorptivity is 0.4 to 2.8 ml/g.

6. The silicate as claimed in claim 1, of which the refractive index is 1.40 to 1.50.

7. The silicate as claimed in claim 1, of which the micropore volume is 0.5 to 6.0 cc/g.

8. A process for producing a synthetic amorphous zirconium-bonded silicate characterized by reacting, as main starting materials, a water-soluble alkali-metal silicate with an inorganic water-soluble zirconyl salt and a mineral acid.

9. The process as claimed in claim 8, characterized by starting the reaction from the alkaline side.

10. The process as claimed in claim 8 wherein the reaction temperature is from 50° to 100° C.

11. The process as claimed in claim 8 wherein the pH at the completion of the reaction is 2 to 8.

12. The process as claimed in claim 8 wherein the use ratio of the $ZrO_2$ of the inorganic water-soluble zirconyl salt to the $SiO_2$ of the water-soluble alkali-metal silicate is in the range of 0.1 to 10 weight %.

13. A process for producing a synthetic amorphous zirconium-bonded silicate characterized by reacting a solution of a water-soluble alkali-metal silicate with a zirconium-containing mineral acid.

14. The process as claimed in claim 13 characterized by starting the reaction from the alkaline side.

15. The process as claimed in claim 13 wherein the zirconium-containing mineral acid is a mixture of a water-soluble zirconyl salt and a mineral acid.

16. The process as claimed in claim 13 wherein the reaction temperature is 50° to 100° C.

17. The process as claimed in claim 13 wherein the pH at the completion of the reaction is 2 to 8.

18. The process as claimed in claim 13 wherein the use ratio of the $ZrO_2$ of the zirconium-containing mineral acid to the $SiO_2$ of the water-soluble alkali-metal silicate is in the range of 0.1 to 10 weight percent.

19. The process as claimed in claim 13 wherein the acid concentration of the zirconium-containing mineral acid is 5 to 15 weight percent.

20. A process for producing a synthetic amorphous zirconium-bonded silicate characterized by reacting a water-soluble alkali-metal silicate solution with a zirconium-containing mineral acid in the presence of an electrolyte.

21. The process as claimed in claim 20 characterized by starting the reaction from the alkaline side.

22. The process as claimed in claim 20 wherein the reaction temperature is 60° to 100° C.

23. The process as claimed in claim 20 wherein the pH at the completion of the reaction is 2 to 8.

24. The process as claimed in claim 20 wherein the amount of the electrolyte present in the reaction system is 5 to 60 weight % based on the $SiO_2$ of the alkali-metal silicate solution.

25. The process as claimed in claim 20 wherein the electrolyte is a mineral acid salt of an alkali-metal.

26. The process as claimed in claim 20 characterized in that the electrolyte is contained in the alkali-metal silicate solution previously.

* * * * *